United States Patent
Sharma et al.

(10) Patent No.: US 6,537,309 B2
(45) Date of Patent: Mar. 25, 2003

(54) REUSABLE HEAT PACK, METHOD OF MANUFACTURE THEREOF, MIXTURE FOR USE IN A REUSABLE HEATPACK AND PROCESS FOR THE PREPARATION THEREOF

(75) Inventors: Chattrapal Sharma, New Delhi (IN); Rajendra Kumar Sharma, New Delhi (IN); Chandra Kant, New Delhi (IN); Ajit Kumar Sarkar, New Delhi (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/817,759

(22) Filed: Mar. 26, 2001

(65) Prior Publication Data

US 2002/0177886 A1 Nov. 28, 2002

(51) Int. Cl.⁷ ................. A61F 7/00; F24J 1/00
(52) U.S. Cl. ............. 607/114; 126/263.01; 126/263.03
(58) Field of Search ............. 607/114, 96; 126/263.01, 126/263.02, 263.03, 263.04, 263.05, 263.06, 263.07, 263.08, 263.09, 263.1, 204; 62/4; 252/67, 69, 70, 71; 383/901

(56) References Cited

U.S. PATENT DOCUMENTS

| 3,661,587 A | * | 5/1972 | Adrian | 430/495.1 |
| 3,913,557 A | | 10/1975 | Dandliker | 126/263 |
| 4,077,390 A | * | 3/1978 | Stanley et al. | 126/263.04 |
| 4,239,018 A | * | 12/1980 | Griffin et al. | 600/551 |
| 4,331,556 A | * | 5/1982 | Arrhenius | 23/296 |
| 4,379,448 A | * | 4/1983 | Kapralis et al. | 126/263.04 |
| 4,451,383 A | * | 5/1984 | Arrhenius | 126/263.03 |
| 4,460,546 A | * | 7/1984 | Kapralis et al. | 126/263.04 |
| 4,532,110 A | * | 7/1985 | Kapralis et al. | 126/263.04 |
| 4,556,640 A | * | 12/1985 | Gantzer | 422/56 |
| 4,572,158 A | | 2/1986 | Fiedler | 126/263 |
| 4,899,727 A | * | 2/1990 | Kapralis et al. | 126/263.04 |
| 4,988,607 A | * | 1/1991 | Ali | 430/271.1 |
| 5,056,589 A | * | 10/1991 | Hettel et al. | 126/263.04 |
| 5,058,563 A | | 10/1991 | Manker | 126/263 |
| 5,205,278 A | * | 4/1993 | Wang | 126/204 |
| RE35,586 E | * | 8/1997 | Manker | 126/263.01 |
| 5,662,096 A | * | 9/1997 | Walters | 126/263.03 |
| 5,736,110 A | * | 4/1998 | Angelillo et al. | 126/263.04 |
| 5,843,145 A | | 12/1998 | Brink | 607/114 |
| 6,283,116 B1 | * | 9/2001 | Yang | 126/263.01 |
| 6,318,359 B1 | * | 11/2001 | Schmidt et al. | 126/263.03 |

FOREIGN PATENT DOCUMENTS

| GB | 2055054 | 2/1981 |
| JP | 58180575 | 10/1983 |

* cited by examiner

*Primary Examiner*—Linda C. M. Dvorak
*Assistant Examiner*—Kenneth G Schopfer
(74) *Attorney, Agent, or Firm*—Ladas & Parry

(57) ABSTRACT

The invention discloses a reusable heat pack comprising a soft sealed plastic bag containing a mixture of supercooled supersaturated recrystalizable solution of inorganic substance, alcohol, chemical compound additives, and means to trigger recrystallization of supercooled supersaturated recrystalizable solution of inorganic substance.

18 Claims, No Drawings

REUSABLE HEAT PACK, METHOD OF MANUFACTURE THEREOF, MIXTURE FOR USE IN A REUSABLE HEATPACK AND PROCESS FOR THE PREPARATION THEREOF

FIELD OF THE INVENTION

The present invention relates to a reusable heat pack. The present invention also relates to a trigger device for a heat pack. The invention also relates to a supercooled supersaturated recrystalizable solution for use in heat pack and to a process for the preparation thereof.

BACKGROUND OF THE INVENTION

Use of heating or cooling for many applications has been done by a variety of techniques depending on the specific need. For example, persons suffering from muscular pains normally use rubber bags filled with hot boiling water to alleviate the pain. In case of any head injury normally the doctor's prescription is to apply ice as a first aid. In case of high fever the common house remedy has been to apply a cloth soaked in cold water on the forehead to bring down the temperature. Many a time on a recreational trip people tend to take packed food or even carry cooking apparatus and the raw, materials for cooking food. The other need of heat energy is in the remote areas where availability of the fuels may not be possible or may be very expensive. Therefore to get over all these difficult situations it is necessary to devise ways and means to generate heat in an economical way and preferably without the use of conventional fuels. To address this very need, development of device called the heat pack has occurred over the past 15 years. The main principle underlying the heat pack is to use heat generated due to a start of a chemical reaction between two or more chemicals or due to triggering of initiation of crystallization of a supercooled chemical solution. In the context of the present invention it is the second aspect which is disclosed Several warming materials are available in the market such as hot water bag, portable electrical bag warmer or battery operated warmer. However, in case of hot water bag, hot water is to be poured in the bag which can only be obtained either by using fuel or electrical energy. Further the heat of the water bag does not last long enough for giving any observable effect. In case of electrical bag warmer a permanent supply of electricity is needed. This limits the use of this heating device to only such places where there is electricity available i.e only indoors. In case of battery operated warmer the battery needs to be charged regularly and needs replacement as and when it gets exhausted. In all these cases another drawback is that the use is very limited and safety precautions need to be taken in case of electrical heat packs.

A non-conventional heat pack has been disclosed in a U.S. Pat. No. 4,532,110(1985). In this disclosure heat energy is generated by a trigger action on a supercooled saturated solution of sodium acetate. The triggering is accomplished by a specially designed device. The entire assembly of trigger and the supercooled solution is kept in a plastic container made of PVC, polyurethane or the like. The drawback in the invention is that the trigger used to initiate the crystallization of the super cooled sodium acetate solution has to have a protective layer of gold or silver to prevent any corrosion due to contact with the chemical. This is not desirable since the material used for the trigger is already an expensive CuBe alloy. Further the PVC material for the heat pack manufacturing has a very limited shelf life due to inevitable leaching of the chloride ion due to the presence of sodium salt solution. This drawback is present in the other disclosed inventions as well as disclosed in U.S. Pat. Nos. 4,572,158; 5,058,563 and 5,205,278. A further drawback in the disclosed inventions, except in U.S. Pat. No. 5,058,563, is that the supercooled solution tends to flow to one side giving rise to uneven heating effects thereby rendering the heat pack difficult to use by needing to adjust the contour of the pack for a particular application before initiation of crystallisation and resultant heat generation.

In U.S. Pat. No. 5,058,563 use has been made of an additive to induce gelation during crystallisation. This gelation helps in maintaining the desired density of the solution and hence uniformity of heat over the entire useful area. The gelation material used in the said disclosure is a water soluble hydroethyl cellulose polymer. This material though giving the advantage of gelling the solution suffers from the disadvantage of being unstable, thereby rendering the heat pack in capable of reuse.

U.S. Pat. No. 5,843,145 discloses a reusable heat pack wherein a mixture of three constituents forming a gel, is sealed in a plastic bag. This reusable heat pack needs an external heating or cooling means to give a useful application of the device. In case of heating application, the heat pack is put in a microwave oven or any other heating means to energise the pack. It is claimed that the temperature of the heat pack is maintained for a sufficient length of time thereby claiming its use as a heat pack. In view of the fact that the pack needs an external heating means, the invention proves to be disadvantageous in its claimed use as a heat pack. This is mainly due to the fact that in the invention discloses that the preconditioning of the pack is to be done for a time period typically two hours. This renders the pack as disclosed not advantageous in an emergency practical situation and also in remote areas, where heating means such as microwave oven may not be available.

JP 58180575 discloses a cooling pack with a mixture provided therein containing inter alia, aniline chloride. However, in this disclosure, the mixture acts as an endothermic material wherein the material when dissolved in water absorbs heat and produces a cooling effect.

The present invention circumvents the drawbacks of the inventions of the prior art.

Objects of the Invention

An object of the present invention is to provide a reusable heat pack which obviates the drawbacks mentioned above.

Another object of the invention is to provide a heat pack with a shelf life of at least six months.

A further objective of the present invention is to provide a heat pack which can be recycled at least a hundred times.

Still another objective of the present invention is to provide a heat pack with heat retention for at least two hours.

Yet another object of the present invention is to provide a heat pack capable of being used for therapeutic application.

SUMMARY OF THE INVENTION

Accordingly the present invention provides a reusable heat pack, which comprises a soft sealed plastic bag containing a mixture of supercooled supersaturated recrystalizable solution of inorganic substance, alcohol, chemical compound additives, and means to trigger recrystallization of supercooled supersaturated recrystalizable solution of inorganic substance.

In an embodiment of the invention the plastic bag is made of polypropylene or polyvinyl chloride.

In another embodiment of the invention, the inorganic substance is selected from sodium acetate and calcium nitrate.

In still another embodiment of the present invention the supercooled supersaturated recrystalizable solution of inorganic substance is made in good quality water.

In a further embodiment of the invention, the good quality water is bacteria free municipal supply or distilled water.

In a further embodiment of the present invention the alcohol is selected from ethylene glycol and glycerol.

In yet another embodiment of the present invention the chemical additive comprises an organic amine.

In a further embodiment of the invention, the organic amine comprises aniline.

In another embodiment of the invention, the supercooled supersaturated recrystalizable solution comprises a mixture of hydrated salt of sodium acetate 50–70 wt %, ethylene glycol 1–10 wt %, aniline 10–20 wt % and water 10–29 wt %.

In another embodiment of the present invention the means for triggering recrystallization comprises a mechanical device selected from the group consisting of crocodile clip and a safety pin.

In a further embodiment of the present invention the material of the means for trigger comprises a noncorrosive material.

In a further embodiment of the invention, the non-corrosive material for the trigger means comprises stainless steel.

In a further embodiment of the invention the heat pack has a shelf life of at least six months.

In still another embodiment of the invention the heat pack is capable of being recycled for at least 100 cycles.

In another embodiment of the present invention the heat pack retains heat for at least two hours.

In still another embodiment of the present invention the heat pack is used for therapeutic applications, body warming in high altitudes.

The invention also relates to a process for the preparation of a reusable heat pack said process comprising preparing a hydrated solution of an inorganic substance in water, adding an alcohol to this solution and mixing thoroughly, adding aniline and thoroughly mixing the resultant mixture, enclosing the mixture in a soft sealed plastic bag and adding a trigger means thereto.

The present invention also relates to a mixture for use in reusable heat packs, said mixture comprising a solution of an inorganic substance in water, alcohol and aniline.

In one embodiment of the invention, the mixture comprises a mixture of hydrated salt of sodium acetate 50–70 wt %, ethylene glycol 1–10 wt %, aniline 10–20 wt % and water 10–29 wt %.

The invention also relates to process for the preparation of a mixture for use in reusable heat packs, said process comprising preparing a hydrated solution of an inorganic substance in water, adding an alcohol to this solution and mixing thoroughly, adding aniline and thoroughly mixing the resultant mixture.

The mixture of the invention for use in a reusable heat pack is a synergistic admixture with properties over and above the aggregation of properties of the individual constituents and is not a simple admixture.

DETAILED DESCRIPTION OF THE INVENTION

First a hydrated solution of preferably sodium acetate of a preferred purity of was prepared in ordinary water by mixing 500–700 g in 0.1 to 0.3 liters of water. The solution was prepared by thoroughly mixing sodium acetate in water. To this was added a polyhydric alcohol and preferably ethylene glycol. this mixture was thoroughly mixed and to this was then added another additive and preferably aniline and the resultant mixture was throughly mixed. The addition of polyhydric alcohol is to provide smoothness to the recrystallized supercooled saturated solution of sodium acetate. This is achieved by controlled increase in viscosity of the resulting mixture after recrystallization due to triggering action by a mechanical device. The use of aniline in the mixture of the heat pack increases the shelf life of the heat pack and also to give the unique property of recyclability of the heat pack. After the mixture has been prepared the same is poured into a plastic bag of preferred dimension of 100 $mm^2$ and made of thin sheet of polyvinyl chloride (PVC). The use of aniline as an additive gives the desired property of preventing the leaching of the plastic material and thereby enhancing the shelf life. A stainless steel crocodile clip is inserted in the heat pack and then finally sealed from the open end. The heat pack is now ready having typical contents, but not limited to, of hydrated salt of sodium acetate 50 wt %, ethylene glycol 1 wt %, aniline 20 wt % and water 29 wt %. The recrystallization activity was initiated by softly pressing the crocodile clip and instantaneously releasing the same. The recrystallization took place and instantaneously heat was generated over the entire heat pack. This heat pack could be easily contoured over a body part and the part warmed thereby. The temperature of the pack was 45° C. above ambient and maintained for about two to three hours depending on the size of the heat pack.

In a typical therapeutic application, after energizing the pack the same is wrapped in a towel and applied on the patient. The cooling of the pack to ambient took place in about four hours time. The pack was reactivated by putting the same in hot water resulting in melting of the crystallized content of the pack and then taking it out from hot water and cooled to ambient temperature. This way the heat pack was ready for use again.

The principle underlying the invention is that the formation of the hydrated salt results in an endothermic reaction absorbing heat of crystallization. When the crystallization is effected by the triggering action the heat of crystallization is released to the container thereby heating the exterior surface of the container. This renders the device useful for any application. The temperature attainable with the heat pack can be fixed by the amount of the supercooled supersaturated solution of the hydrated salt. Accordingly the shelf life of the device will also be adjusted by correspondingly increasing the quantity of the aniline or any of the other additives like hydroxides or carbonates.

The novelty of the present invention lies in the heat pack being reusable and having a long shelf life and being recyclable.

This novelty of the heat pack is due to the inventive step of adding hydroxides, carbonates or amines to the recrystallizable mixture.

In the embodiment of the examples the heat pack is manufactured by first dissolving hydrated salt of sodium acetate in water. Ethylene glycol was added to this. This was mixed thoroughly and to this aniline was added. Again the mixture was thoroughly mixed and then poured in a plastic bag of PVC. The trigger used is a stainless steel crocodile clip and is put inside the bag and then the whole assembly was sealed.

The following examples are given by way of illustration only and should not be construed to limit the scope of the invention.

EXAMPLE 1

Heat pack contained hydrated salt of sodium acetate 50 wt %, ethylene glycol 1 wt %, aniline 20 wt % and water 29 wt %. Triggering action was done by pressing the clip three times. The crystallization resulted in instantaneous temperature rise to 75° C. The cooling of the pack to reach to ambient temperature took place in about four hours time.

EXAMPLE 2

Heat pack contained hydrated salt of sodium acetate 60 wt %, ethylene glycol 4wt %, aniline 15 wt % and water 21 wt %. The triggering action was done by pressing the clip three times. The crystallization resulted in instantaneous temperature rise to 65° C. The cooling of the pack to reach to ambient temperature took place in about four hours time.

EXAMPLE 3

Heat pack contained hydrated salt of sodium acetate 70 wt %, ethylene glycol 6wt %, aniline 10 wt % and water 14 wt %. The triggering action was done by pressing the clip three times. The crystallization resulted in instantaneous temperature rise to 75° C. The cooling of the pack to reach to ambient temperature took place in about four hours time.

EXAMPLE 4

Heat pack contained hydrated salt of sodium acetate 70 wt %, ethylene glycol 10 wt %, aniline 10 wt % and water 10 wt %. The triggering action was done by pressing the clip three times. The crystallization resulted in instantaneous temperature rise to 70° C. The cooling of the pack to reach to ambient temperature took place in about four hours time. Table 1 shows the consolidated results of the examples.

TABLE 1

| Item | Weight percent of materials | | | |
|---|---|---|---|---|
| Sodium acetate | 50 | 60 | 70 | 70 |
| Ethylene Glycol | 1 | 4 | 6 | 10 |
| Aniline | 20 | 15 | 10 | 10 |
| Water | 29 | 21 | 14 | 10 |
| Temp of Heat pack ° C. | 75 | 65 | 75 | 70 |

The main advantages of the present invention are:
1. It is easy to manufacture from commonly available chemicals and of moderate purity.
2. The heat pack can be stored for at least six months
3. The pack can be easily put on any contour due to its being flexible even after re crystallization.

We claim:

1. A reusable heat pack, comprising (a) a plastic bag; (b) a mixture of supercooled supersaturated recrystalizable solution in the plastic bag; said solution comprising an inorganic substance, an alcohol, and an aniline; and (c) means for triggering recrystallization of the supercooled supersaturated recrystalizable solution within the bag.

2. A reusable heat pack as claimed in claim 1, wherein the plastic bag is made of polypropylene or polyvinyl chloride.

3. A reusable heat pack as claimed in claim 1, wherein the inorganic substance is selected from the group consisting of sodium acetate and calcium nitrate.

4. A reusable heat pack as claimed in claim 1, wherein the supercooled supersaturated recrystalizable solution of inorganic substance is made in substantially pure water.

5. A reusable heat pack as claimed in claim 4, wherein the substantially pure water comprises bacteria free municipal supply or distilled water.

6. A reusable heat pack as claimed in claim 1, wherein the alcohol is selected from the group consisting of ethylene glycol and glycerol.

7. A reusable heat pack as claimed in claim 1, wherein the supercooled supersaturated recrystalizable solution comprises a mixture of hydrated salt of sodium acetate in an amount 50–70 wt %, ethylene glycol in an amount of 1–10 wt %, aniline in an amount of 10–20 wt % and water in an amount of 10–29 wt %.

8. A reusable heat pack as claimed in claim 1, wherein the means for triggering comprises a mechanical device selected from the group consisting of a crocodile clip and a safety pin.

9. A reusable heat pack as claimed in claim 1, wherein the means for triggering comprises a non-corrosive material.

10. A reusable pack as claimed in claim 5, wherein the non-corrosive material comprises stainless steel.

11. A reusable heat pack as claimed in claim 1, wherein the plastic bag is made of polyvinyl chloride and the aniline is present in the solution in an amount sufficient to inhibit leaching of the polyvinyl chloride from the plastic bag.

12. A method for generating heat upon demand comprising:
(a) providing the heat pack of claim 1; and
(b) initiating recrystallization of the supercooled supersaturated recrystalizable solution in the plastic bag by manipulation of the triggering means.

13. The method according to claim 12, wherein the triggering means comprises a clip or a pin.

14. A supercooled supersaturated recrystalizable solution for use in a heat pack, said supercooled super saturated recrystallisable solution comprising solution of an inorganic substance, alcohol and aniline.

15. A supercooled supersaturated recrystalizable solution as claimed in claim 7, comprising a mixture of hydrated salt of sodium acetate in an amount of 50–70 wt %, ethylene glycol in an amount of 1–10 wt %, aniline in an amount of 10–20 wt % and water in an amount of 10–29 wt %.

16. A process for the preparation of a mixture for use in reusable heat packs, said process comprising preparing a hydrated solution of an inorganic substance in water, adding an alcohol to the solution and mixing thoroughly, adding aniline to form a resultant mixture and thoroughly mixing the resultant mixture.

17. A method for the manufacture of a reusable heat pack, said process comprising preparing a hydrated solution of an inorganic substance in water, adding an alcohol to the solution and mixing thoroughly, adding aniline and thoroughly mixing to form a resultant mixture that is recrystalizable, enclosing the resultant mixture in a sealed plastic bag and adding thereto a trigger means for triggering recrystallization of the resultant mixture.

18. A method for the manufacture of a reusable heat pack said process comprising preparing a hydrated solution of an inorganic substance in water, adding an alcohol to this solution and mixing thoroughly, adding aniline and thoroughly mixing the resultant mixture, enclosing the mixture in a soft sealed plastic bag and adding a trigger means thereto.

* * * * *